United States Patent
Holmes et al.

(10) Patent No.: US 10,179,102 B2
(45) Date of Patent: Jan. 15, 2019

(54) HAIR CONDITIONER FOR WAVY AND CURLY HAIR

(71) Applicant: Kao USA, Inc., Cincinnati, OH (US)

(72) Inventors: Chris Holmes, Cincinnati, OH (US); Adam Schrott, Cincinnati, OH (US)

(73) Assignee: Kao USA, Inc., Cincinnati, OH (US)

( * ) Notice: Subject to any disclaimer, the term of this patent is extended or adjusted under 35 U.S.C. 154(b) by 0 days.

(21) Appl. No.: 15/393,508

(22) Filed: Dec. 29, 2016

(65) Prior Publication Data

US 2018/0185264 A1 Jul. 5, 2018

(51) Int. Cl.
*A61K 8/85* (2006.01)
*A61K 8/58* (2006.01)
*A61Q 5/12* (2006.01)
*A61K 8/41* (2006.01)

(52) U.S. Cl.
CPC ............... *A61K 8/85* (2013.01); *A61K 8/416* (2013.01); *A61K 8/585* (2013.01); *A61Q 5/12* (2013.01)

(58) Field of Classification Search
None
See application file for complete search history.

(56) References Cited

U.S. PATENT DOCUMENTS

| | | | | |
|---|---|---|---|---|
| 6,706,674 B2 * | 3/2004 | Cincotta | ............... | A61K 8/8182 424/401 |
| 2010/0047202 A1 * | 2/2010 | Goddinger | ............. | A61K 8/731 424/70.12 |
| 2010/0218781 A1 * | 9/2010 | McNamara | ............ | A45D 40/26 132/200 |
| 2011/0293551 A1 * | 12/2011 | Molenda | .................. | A61K 8/06 424/70.9 |

* cited by examiner

*Primary Examiner* — Ernst V Arnold
*Assistant Examiner* — Kyung S Chang
(74) *Attorney, Agent, or Firm* — Frost Brown Todd, LLC

(57) ABSTRACT

The present application discloses hair conditioning compositions which provide effective hair conditioning, particularly to wavy or curly hair, the conditioning benefit lasting in the hair over several (up to 10) subsequent shampooings. The compositions comprise a film-forming polyester that is the reaction product of at least one diol, at least one polyol, and at least one dicarboxylic acid; polyquaternium-52 and/or polyquaternium-37; and at least one amino or aminopropyl-functional silicone, in an aqueous vehicle. The composition may additionally include dimethicone and/or a branched-chain ester. The method of conditioning hair using the defined compositions is also disclosed.

16 Claims, No Drawings

100 # HAIR CONDITIONER FOR WAVY AND CURLY HAIR

BACKGROUND

The present invention relates to a hair conditioner composition which is particularly well-adapted for use on wavy and/or curly hair.

Shampooing hair has become a regular part of the typical personal care regimen. Frequent shampooing, by removing at least some of the natural oils in hair, results in an increased need to condition that hair so that it can be combed and styled. Conditioning enhances the tactile properties of the hair (smoothness and softness); it assures that hair is tamed and well-behaved (free from frizz), and that the hair is controllable when styled. This can be a particular problem with hair that is naturally wavy and/or curly. The present invention is unique in that it not only delivers these benefits, but delivers them such that they last through multiple shampoos (3-10 shampoos). The present invention therefore provides these conditioning benefits with very high wash durability.

The composition of the present invention utilizes a film-forming polyester, a suspending agent selected from polyquaternium-52 and polyquaternium-37, and an amino or aminopropyl-functional silicone. While each of these three components is known for use in and of itself for use in hair care products, the hair care compositions of the present invention, by combining the three components, provides these unexpected conditioning and wash durability benefits, discussed above.

Existing hair conditioning products are typically leave-on products which provide a conditioning benefit through the application of:
  silicones, quaternary ammonium materials, esters, hydrocarbons and/or natural oils which can result in a greasy feel and weigh down hair; and/or
  styling polymers which can give hair an undesirable unnatural feel and a "wet" look.

The typical existing conditioning product also only provides transient benefits that do not last through even the next shampoo, much less through multiple shampoos, therefore requiring reapplication after each wash cycle. The closest known products to the present invention are thought to be styling lotions and creams that provide a mix of conditioning and hold, but these products are for daily use, and their benefits are not durable through multiple hair washes.

SUMMARY

The present invention relates to an aqueous cosmetic composition for application to hair comprising:
(a) at least one film-forming polyester that is a reaction product of at least one diol, one polyol, and one dicarboxylic acid (such as trimethylpentanediol/adipic acid/glycerin crosspolymer);
(b) at least one suspending agent selected from polyquaternium-52, polyquaternium-37, and mixtures thereof; and
(c) an amino or aminopropyl-functional silicone (such as bis-hydroxy/methoxy amodimethicone).

The present invention also relates to the method of conditioning hair using this composition wherein the composition is applied to wet or dry hair, left on the hair for from about 1 to about 10 minutes, and then shampooed out of the hair. This treatment not only provides excellent hair conditioning properties, particularly noticeable with respect to wavy and curly hair, but those properties are durable, lasting for multiple shampoos (e.g., from about 3 to about 10 shampoos).

All percentages and ratios described herein are "by weight", unless otherwise specified. Further, any patents, patent applications or other publications cited in this application are incorporated by reference in this application.

DETAILED DESCRIPTION

The present invention relates to an aqueous hair conditioner composition including a film-forming polyester which is the reaction product of at least one diol, one polyol, and one dicarboxylic acid; a suspending agent selected from polyquaternium-52 and/or polyquaternium-37; and an amino or aminopropyl-functional silicone. These materials are all well-known in the hair care art and will be discussed in more detail below.

The film-forming polyester component of the present invention is used at a level of from about 0.5 to about 15%, for example, from about 1% to about 5%, of the hair conditioner composition. The polyester is formed by the polyesterification reaction of at least one diol, at least one polyol, and at least one dicarboxylic acid. Typical diacids include adipic acid and dodecanoic acid. Typical polyols include trimethylolpropane, trimethylolethane, pentaerythritol and dipentaerythritol. Typical diols include ethylene glycol, propylene glycol, diglycol, 1,3-butylene glycol, 1,4-butanediol, neopentyl glycol, 1,6-hexanediol, dipropylene glycol, trimethyl pentanediol, and polyoxyalkylene glycols. These film-forming polyester materials are well-known and have been used in both hair care products and cosmetic products. It is preferred that the diol used in making the polyester has a backbone which includes from 3 to 10 carbon atoms. Examples of specific polyester materials useful in the present invention include trimethylpentanediol/adipic acid/glycerin crosspolymer, adipic acid/dilinoleic acid/hexylene glycol copolymer, and trimethylpentanediol/adipic acid/isononanoic acid copolymer. A particular example of these polymers for use in the present invention is trimethylpentanediol/adipic acid/glycerine crosspolymer. Examples of these materials are commercially available from Inolex Chemical Co., Philadelphia, Pa., under the trade name WetFilm and Lexorez®.

The second component utilized in the compositions of the present invention is at least one suspending agent selected from polyquaternium-52, polyquaternium-37, and mixtures thereof. These polyquaternium materials are well-known for use in personal care compositions. They are used in the present invention at from about 0.5% to about 5% of the composition. Polyquaternium-37 is a poly(2-methyacryloxyethyltrimethylammonium chloride) and is commercially available, for example, as Salcare SC96 from BASF. Polyquaternium-52 is chemically described as 2-(N,N-dimethylamino) ethyl 2-methyl-2-propanoate, polymerized with N,N-dimethyl-2-propanamide and C1-C30 acylpoly (oxyethylene) 2-methyl-2-propenoate, quaternized with diethyl sulfate. Polyquat-52 is commercially available, for example, as Merquat 5210 from Lubrizol. These materials are well-known for use in personal care and cosmetic products. A material used frequently in the compositions of the present invention is polyquat-37.

The third component utilized in the present invention is an amino or aminopropyl-functional silicone present at from about 0.5% to about 10%, such as from about 1% to about 5%, of the final composition. Amino-functionalized silicones is a family of silicones modified to have specific properties. The simplest, and perhaps most well-known silicone, polydimethylsiloxane (dimethicone), consists of methyl groups (—CH₃) as the pendant group along the backbone of the polymer chain. Amino-functionalized silicones have been chemically modified so that some of the pendant groups along the backbone have been replaced with various alkylamine groups (—R—NH₂). These amine groups become positively charged in aqueous solutions because of their electron-donating (basic) tendencies, yielding an inorganic cationic polymer. These inorganic cationic polymers deposit onto the hair because of the electrostatic attraction between the positively-charged polymers and the hair itself. The charge density of these polymers can be varied by changing the placement and quantity of the amine groups. A polymer with greater charge density will be more substantive to the hair than one with lesser charge density. Amodimethicones generally have the following structural formula

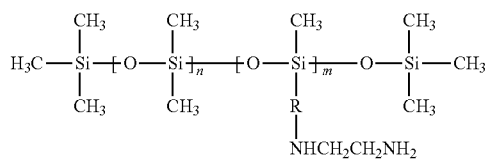

Aminopropyl functional silicones are similar to those in the above structural formula except that instead of using amine groups, aminopropyl functional groups are utilized. Amino-functional silicones have been known for use in hair care products, including conditioners, providing conditioning, shine and combing performance. Examples of amino-functional silicones utilized in the present invention include bis-hydroxy/methoxy amodimethicone, bis-cetearyl amodimethicone, and amodimethicone, as well as mixtures of those materials. An amino-functional silicone frequently used in the present invention is bis-hydroxy/methoxy amodimethicone.

In the compositions of the present invention, the weight ratio of the film-forming polymer:amino-functional silicone is typically from about 5:1 to about 1:3, for example, from about 2:1 to about 1:1.

The composition of the present invention is an aqueous composition and so it contains an aqueous solvent which comprises water or a water/alcohol (such as a water/ethanol) mixture. Typically, the composition contains from about 70% to about 98% water, such as from about 80% to about 95% water.

The compositions defined herein may also contain optional components which are typically found in hair care and particularly hair conditioner compositions. Thus, for example, the present invention may contain a polydimethylsiloxane (also known as dimethicone) component to act as a hair conditioning material. Dimethicone or polydimethylsiloxane (PDMS) belongs to a group of polymeric organosilicon compounds that are commonly referred to as silicones. PDMS is the most widely-used silicone-based organic polymer, and is particularly-known for its unusual rheological (or flow) properties. It is also called dimethicone and is one of several types of silicone oil (polymerized siloxane). It is frequently used in hair care compositions, such as shampoos and conditioners, to make hair shiny or slippery. When used, the dimethicone component is present in the compositions of the present invention at from about 1% to about 15%, such as from about 1% to about 5%. The dimethicone materials used typically have a viscosity of from about 100 to about 10,000 centistokes. Low viscosity dimethicones are preferred (such as those having a viscosity of about 350 cs). The PDMS materials have a structural formula as follows:

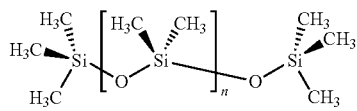

Another component that may optionally be included in the compositions of the present invention are branched-alkyl esters which are well-known to act as an emollient and, when present, are used at levels of from about 1% to about 10%, such as from about 1% to about 5%, of the total composition. These materials can also act as a dispersant for the polyquaternium material. These materials typically are esters of branched-chain alcohols with a long chain fatty acid. Examples of such branched-chain esters include isopropyl palmitate, isopropyl myristate, isocetyl stearate, isostearyl stearate, and tricaprylin (a glyceryl ester), as well as combinations of these materials.

The compositions of the present invention may also include conventional additives which are typically used in hair care compositions, at their conventional usage levels, as long as those additives are compatible with the other components of the composition and do not detract from the beneficial results delivered by the present invention. Additives which may be used in various compositions include waxes, other oils and fats and derivatives thereof, fatty acid esters of varying chain lengths, synthetic oils and fats, polymers, alcohols, polyhydric alcohols, extracts useful for providing fragrance, amino acids, nucleic acids, vitamins, hydrolyzed proteins and derivatives thereof, glycerin and derivatives thereof, enzymes, anti-inflammatory agents and other medicaments, microbiocides, anti-fungals, antiseptics, antioxidants, UV absorbers, dyes and pigments, sunscreen active agents, chelating agents, oxidizers, pH balancing agents, moisturizers and the like, approved for topical use in formulations for human use. In addition, additives such as EDTA, glutamic acid, glycerin, panthenol, cyclomethicone, and pH adjustment additives may be included.

Examples of metal ion sequestering agents include 1-hydroxyethane-1,1-diphosphonic acid, 1-hydroxyethane-1,1-diphosphonic acid, 4Na salt, disodium edetate, trisodium edetate, tetrasodium edetate, sodium citrate, sodium polyphosphate, sodium metaphosphate, gluconic acid, phosphoric acid, citric acid, ascorbic acid, succinic acid, edetic acid, and trisodium hydroxyethyl ethylenediamine triacetate.

Examples of vitamins which may be included in the compositions of the present invention include vitamins A, B1, B2, B6, C and E and derivatives thereof; pantothenic acid and derivatives thereof; and biotin.

Examples of antioxidants include tocopherols, dibutylhydroxytoluene, butylhydroxyanisole and gallic acid esters. Examples of antioxidant acids include phosphoric acid, citric acid, ascorbic acid, maleic acid, malonic acid, succinic acid, lactic acid, fumaric acid, cephalin, hexametaphosphate, phytic acid, and ethylenediaminetetraacetic acid.

Various fragrances, fragrance components, and colorants may be included to provide desirable aesthetics for the compositions of the present invention.

Typical examples of germ inhibitors, which are used as preservatives acting specifically against gram-positive bacteria include 2, 4, 4'-trichloro-2'-hydroxyldiphenyl ether, chlorhexidine (1,6-di-(4-chlorophenyl-biguano)-hexane or TCC (3,4,4'-trichlorocarbonilide). Numerous perfumes and essential oils also have antimicrobial properties. Typical examples of such materials include eugenol, menthol and thymol in clove, mint and thyme oil.

The compositions of the present invention can be made using the following protocol: with the exception of the fragrance and preservative components, the ingredients of the present compositions are combined at a temperature of from about 70° C. to about 90° C. with adequate mixing until homogeneous. The product is then cooled, with mixing, to a temperature of less than 40° C., prior to incorporating the fragrance and preservative components. The composition is then mixed until homogeneous. However, it should be noted that the compositions of the present invention can also be made by combining the defined ingredients without heating.

The compositions of the present invention are used to condition hair. In use, the conditioner compositions of the present invention (in an "effective amount") are applied to wet (i.e., shampooed) or dry hair, left on the hair for from about 1 to about 10 minutes and is then removed from the hair, such as by shampooing the conditioner from the hair. The hair is then dried, for example, either air dried or using a blow dryer. As used herein, the term "effective amount" is an amount of the composition of the present invention in a sufficient quantity to provide adequate conditioning when worked into the hair, but which is not such a high level as to cause any undesirable effects to the hair, skin or eyes. The average amount of product required for application depends on whether it is being applied to wet or dry hair. For wet hair, between about 1 and about 20 grams are applied, with the average being around 10 grams. For dry hair, the amount applied typically increases and falls between about 40 and about 60 grams. Wet application typically will provide a stepwise increase in benefit with each use. On the other hand, dry application typically provides a full benefit in a single use.

EXAMPLES

The following examples illustrate the compositions of the present invention, as well as the use of those compositions to provide hair conditioning.

Example 1

|   |   | Weight % |
|---|---|---|
| A | Water | 86.930 |
| B | Isopropyl Palmitate | 3.000 |
|   | Polyquaternium-37 | 1.000 |
| C | Dimethicone | 3.000 |
|   | Bis-Hydroxy/Methoxy Amodimethicone | 1.000 |
|   | Water (and) Silicone Quaternium-18 (and) Trideceth-6 (and) Trideceth-12 | 4.000 |
|   | Trimethylpentanediol (and) Adipic Acid (and) Glycerine Copolymer | 1.000 |
| D | Methylchloroisothiazolinone (and) Methylisothiazolinone | 0.070 |

The composition above is made by combining the ingredients listed, in the order listed, at a temperature of from about 70 to about 90° C. with adequate mixing until homogeneous. Any fragrance and preservative components are not included in this initial mixing or combination of ingredients. The product is then cooled, with mixing, to a temperature of less than 40° C., prior to incorporating the fragrance and preservative components. The final composition is then mixed until homogeneous.

In use, the consumer shampoos their hair thoroughly and then applies about 10 g. of the above composition to the wet hair, working it through the hair with their fingers. The composition is left in the hair for about one minute and is then rinsed out of the hair with water. The hair is first towel-dried and then dried and styled with a blow dryer. The composition acts to condition the hair. That hair conditioning benefit lasts through four subsequent shampooings.

Example 2

|   |   | Weight % |
|---|---|---|
| A | Water | 90.930 |
| B | Isopropyl Palmitate | 3.000 |
|   | Polyquaternium-37 | 1.000 |
| C | Dimethicone 350 cs | 3.000 |
|   | Amodimethicone | 1.000 |
|   | Trimethylpentanediol (and) Adipic Acid (and) Glycerine Copolymer | 1.000 |
|   | Methylchloroisothiazolinone (and) Methylisothiazolinone | 0.070 |

The above composition is made as described for Example 1.

In use, the consumer wets their hair thoroughly and then applies about 10 g. of composition #2 to the hair, working it through the hair with their fingers. The composition is allowed to stay on the hair for about two minutes and is then rinsed out of the hair with water. The hair is then towel-dried and then dried and styled with a blow dryer. The composition of the present invention conditions the hair effectively. This conditioning effect lasts through three subsequent shampooings of the hair.

What is claimed is:

1. An aqueous cosmetic composition for application to the hair comprising:
    (a) at least one film-forming polyester that is a reaction product of at least one diol, at least one polyol and at least one dicarboxylic acid, wherein said at least one film-forming polyester is trimethylpentanediol/adipic acid/glycerine crosspolymer;
    (b) at least one suspending agent selected from the group consisting of polyquaternium-52, polyquaternium-37, and mixtures thereof; and
    (c) at least amino or aminopropyl-functional silicone.

2. The cosmetic composition according to claim 1, wherein the at least one diol has a C3 to C10 backbone.

3. The cosmetic composition according to claim 1, wherein said at least one film-forming polyester is present in the composition in an amount of from about 1% to about 15%.

4. The cosmetic composition according to claim 3, wherein said at least one film-forming polyester is present in the composition at from about 1% to about 5%.

5. The cosmetic composition according to claim 1, wherein said suspending agent is polyquaternium-37.

6. The cosmetic composition according to claim 1, wherein the aminopropyl functional silicone is selected from the group consisting of bis-hydroxy/methoxy amodimethicone, bis-cetearyl amodimethicone, amodimethicone, and mixtures thereof.

7. The cosmetic composition according to claim 6, wherein said aminopropyl functional silicone is bis-hydroxy/methoxy amodimethicone.

8. The cosmetic composition according to claim 1, which additionally contains from about 1% to about 15% dimethicone.

9. The cosmetic composition according to claim 8, wherein said dimethicone has a viscosity of from about 100 to about 10,000 centistokes.

10. The cosmetic composition according to claim 1, which additionally contains from about 1% to about 10% of a branched-ester.

11. The cosmetic composition according to claim 10, wherein the branched-ester is isopropyl palmitate.

12. The cosmetic composition according to claim 1, wherein the weight ratio of said film-forming polyester to said aminopropyl-functional silicone is from about 5:1 to about 1:3.

13. The cosmetic composition according to claim 12, wherein the weight ratio of said film-forming polyester to said aminopropyl-functional silicone is from about 2:1 to about 1:1.

14. The method of treating hair comprising adding to hair an aqueous cosmetic composition according to claim 1, in an effective amount, allowing that composition to remain on the hair for from about 1 to about 10 minutes, and rinsing said composition out of the hair using water.

15. The method of treating hair according to claim 14, wherein the aqueous cosmetic composition is applied to dry hair, and from about 40 to about 60 grams of the composition is applied.

16. The method of treating hair according to claim 14, further comprising treating said hair with a shampoo prior to treatment with said aqueous cosmetic composition, and wherein from about 1 to about 20 grams of the composition is applied.

* * * * *